(12) United States Patent
Grabmaier et al.

(10) Patent No.: US 6,373,215 B1
(45) Date of Patent: Apr. 16, 2002

(54) DEVICE FOR MONITORING THE STATE OF A WINDOW PANE

(75) Inventors: Anton Grabmaier; Martin Osterfeld, both of Bietigheim-Bissingen (DE)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 09/600,333

(22) PCT Filed: Jan. 11, 1999

(86) PCT No.: PCT/EP99/00102

§ 371 Date: Jul. 13, 2000

§ 102(e) Date: Jul. 13, 2000

(87) PCT Pub. No.: WO99/37512

PCT Pub. Date: Jul. 29, 1999

(30) Foreign Application Priority Data

Jan. 20, 1998 (DE) .......................... 198 01 745

(51) Int. Cl.[7] ............................ G05B 5/00; H02H 7/08; H02P 1/04; H02P 3/00; H02P 7/00
(52) U.S. Cl. .................... 318/483; 318/DIG. 2
(58) Field of Search ................ 318/483, 444, 318/480, DIG. 2

(56) References Cited

U.S. PATENT DOCUMENTS

| | | | |
|---|---|---|---|
| 5,059,877 A | 10/1991 | Teder | 318/444 |
| 5,237,249 A * | 8/1993 | Levers | 318/443 |
| 5,313,072 A * | 5/1994 | Vachss | |
| 5,386,111 A | 1/1995 | Zimmerman | 250/227 |
| 6,084,519 A * | 7/2000 | Coulling et al. | |
| 6,118,383 A * | 9/2000 | Hegyi | |
| 6,232,603 B1 * | 5/2001 | Nelson | |
| 6,239,444 B1 * | 5/2001 | Tanaka et al. | |

FOREIGN PATENT DOCUMENTS

| | | |
|---|---|---|
| DE | 31 08234 | 3/1981 |
| DE | 36 19209 | 6/1986 |
| DE | 37 15798 | 5/1987 |
| DE | 38 25 663 | 7/1988 |
| DE | 41 23 641 | 7/1991 |
| DE | 43 18 358 | 5/1993 |
| DE | 93 09 837 | 7/1993 |
| DE | 43 40 681 | 11/1993 |
| DE | 44 01 755 | 1/1994 |
| EP | 0 312 788 | 9/1988 |
| JP | 01025036 | 1/1989 |

OTHER PUBLICATIONS

"Optical Rain Sensor"; *SPIE Web OE Reports*; Online News for the Optomechanical and Precision Instrument Design Working Group; vol. 168, Dec. 1997.

"Fog Sensor"; *Control Devices, Inc.* Innovative Solutions; May 1999; retrieved from Internet::url:http://www.controldevices.com/fog.htm.

Grunbecken,A.: Scheibenwischersteuerung mit Einschaltautomatik. In: Elektronik 1992, H.1, S.17–19; Abschnitt 3.1.

* cited by examiner

*Primary Examiner*—Jeffrey Donels
(74) *Attorney, Agent, or Firm*—J. Gordon Lewis

(57) ABSTRACT

A device for monitoring the state of a window pane includes an optical emitter which emits a light beam on to the window pane. The device also contains an optical receiver which detects light of the light beam modulated by the window pane and, as a result, generates a received signal. The emitter and the receiver are arranged at a distance from the window pane. An evaluation circuit evaluates the received signal in order to determine the state of the window pane.

20 Claims, 5 Drawing Sheets

DEVICE FOR MONITORING THE STATE OF A WINDOW PANE

BACKGROUND

The invention pertains to a device for monitoring the state of a window pane, in particular, an automobile window pane, consisting of at least one optical transmitter which emits a light beam onto a pane, at least one optical receiver which receives the light of the light beam modulated by the pane and subsequently generates a reception signal, and an evaluation circuit that evaluates the reception signal to determine the state of the pane.

The comfort and safety of a motor vehicle can be enhanced by automatic operation of the windshield wiper system. Usually, optical rate sensors located directly on the inside of the pane are used for this purpose. The state of the window pane on the outside of the pane is detected by the sensor through the pane. The monitored region in this case is limited by the size of the sensor and is less than the field of view of the driver.

SUMMARY

The present invention is based on the task of creating a device for monitoring the state of a window pane which can be flexibly adapted to different operating situations and which allows a dependable determination of the state of the window pane.

The task is achieved in that the transmitter and the receiver are located at a distance from the window pane.

Due to this distant placement of both the transmitter and the receiver from the pane, the advantage achieved is that the size of the monitored region can be selected independently of the dimensions of the device. An additional advantage consists in that the location of the monitored region can be largely user-selected and can be located, for example, in the immediate field of view of an automobile driver. Due to the potential for prior specification of a suitable size and location of the monitored region, the dependability of the attainable evaluation result can be improved significantly.

Even though the measurement can also theoretically take place during transmission, the receiver preferably detects the light of the transmitter through reflection or scattering off the pane. A sufficiently large monitored region with simultaneously good intensity of the reflected light can be attained when the transmitter and the receiver are located at a distance of about 10 to 30 cm from the pane.

Preferably the light spot projected onto the pane by the light beam has a surface area of at least 25 cm$^2$ and preferably about 100 cm$^2$. The general state of the pane will then be represented in sufficient measure by the reflected light, and local changes in the state of the pane due to, for example, an area of dirt or a single, large rain drop, are not problems because of the size of the monitored region and they cannot falsify the monitored result, as is the case for sensors which are located directly on the glass and thus necessarily have a small monitored region.

The value of the monitored result will be increased when the state of the window pane that is being monitored is in the region of the immediate field of view of a driver.

Preferably, the transmitter operates in the infrared range, because this will prevent a driver or another person that is looking through the pane from being adversely affected by interfering reflections. Furthermore, it is an advantage that low-cost optical-electronic components operating in the infrared range, such as Si-photodiodes (as the receiver) and infrared LEDs (as the transmitter) are available.

According to one preferred design format of the present invention, the device is composed of a number of optical transmitters. Due to several optical transmitters, a greater transmission power can be achieved, so that the distance between the sensor and the pane can be increased. This makes possible more favorable monitoring geometries and, in addition, allows the angle between the optical axis of the transmitter and receiver, respectively, and the pane to be selected as more flat.

Even though basically several optical receivers can be provided, one preferred embodiment is characterized in that the device is composed of only one optical receiver.

In the case of several optical transmitters and one single receiver, one favorable embodiment of the invented evaluation circuit is characterized in that the circuit is composed of a discriminator stage which uses the reception signal to derive a first and a second reception signal according to the acquired modulated light from one or more first and one or more second optical transmitters. Due to this property, a transmitter-specific and, thus, also light-spot-specific, evaluation of the reception signal provided by the single receiver will be possible, which in practice allows a simultaneous monitoring of different regions of the window pane.

One simple possibility for forming the first and the second reception signals consists in that the first and second optical transmitter is controlled by a pulse signal of different phase and the discriminator stage is composed of a phase-synchronous demodulator.

Preferably, the evaluation circuit is composed of a difference stage which forms a difference signal from the first and the second reception signals. Different states of the window pane can be recognized from the temporal change in behavior of the difference signal. Whereas adhered dirt or even damage to the window pane will cause sudden, static changes, fast changes are caused by large raindrops and slow changes by smaller raindrops. Based on the state of the window pane detected in this manner, additional measures can be undertaken, such as, for example, the regulation of the speed of the windshield wipers.

A particularly compact design of the invented device is attained when the transmitter and the receiver are located in a common module or housing.

According to one preferred configuration of the present invention, on the input side of the optical receiver there is a reception lens which concentrates the light modulated by the pane onto the receiver. Due to this property, the sensitivity of the reception device will be increased and thus a greater distance between the sensor and the pane will be possible.

Due to the reception lens, a reception zone will be defined on the window pane. With regard to attaining the greatest measurement sensitivity, it is preferable to design the reception lens so that a reception zone defined on the pane by the reception lens matches the illuminated zone formed on the pane by the light spots of the light beam.

Due to the optical filter located on the input side in front of the optical receiver, interference caused by incident, secondary light can be prevented as long as the secondary light has a different wavelength than the transmitted light. In the case of a sensor operating in the infrared range, visible, scattered light can thus be effectively excluded as a potential source of interference.

BRIEF DESCRIPTION OF THE DRAWING

The invention will be described in greater detail below based on the following figures and examples.

DETAILED DESCRIPTION

Figure 1:
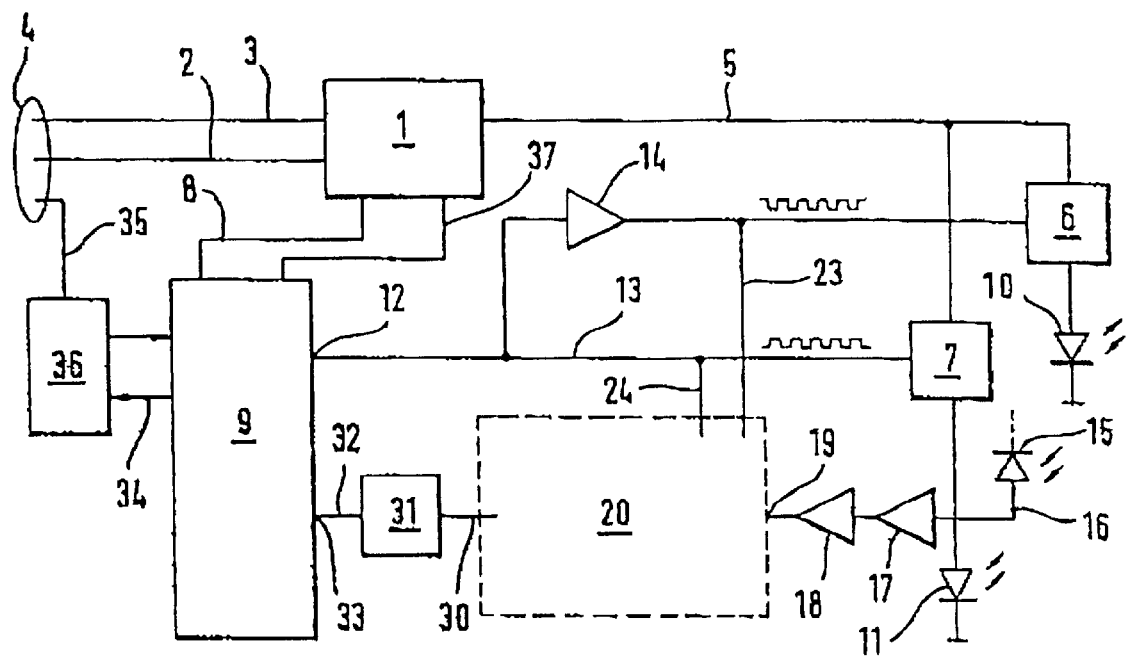
FIG. 1 is a schematic illustration of one circuit design of one embodiment of the present invention.

According to FIG. 1, a device according to this invention has an internal voltage supply 1 which is connected by means of power supply lines 2,3 to an external power supply (not illustrated in FIG. 1), for example, the on-board power supply of a motor vehicle. Reference number 4 denotes an opening in the housing. The internal power supply 1 powers two switching power sources 6 and 7 via a power supply line 5 and powers a microcontroller 9 via a power supply line 8. The switching power supplies 6 and 7 are connected electrically on the output side to a first optical transmitter 10 and to a second optical transmitter 11, respectively. The optical transmitters 10,11 operate in the infrared range and can be designed, for example, with III–V semiconductor LEDs.

The control of the optical transmitters 10,11 takes place by means of the microcontroller 9. A pulse signal with a frequency of 50 kHz, for example, is available to a digital output 12 of the microcontroller 9. The pulse signal is sent directly to the switching input of the power supply 7 via a control line 13, but it reaches the switched input of the power supply 6 only after passing through a 180° inverter 14. The switching signal output from the inverter 14 is thus phase-shifted by 180° to the switching signal in the control line 13, which means that the switching power supplies 6,7 are alternately switched on and off and the optical transmitters 10,11 are thus operated alternately.

The light emitted from the transmitters 10,11 moves to a window pane (not illustrated in FIG. 1) and is reflected from the window pane (in a manner to be described below) onto a receiver 15. The receiver 15 can be designed with a Si-photodiode, for example.

The reception signal 16 output from the receiver 15 is amplified by an amplifier 17 and then passes through a bandpass filter 18. The output signal 19 of the bandpass filter 18 is sent to a signal processing circuit 20.

Figure 2:
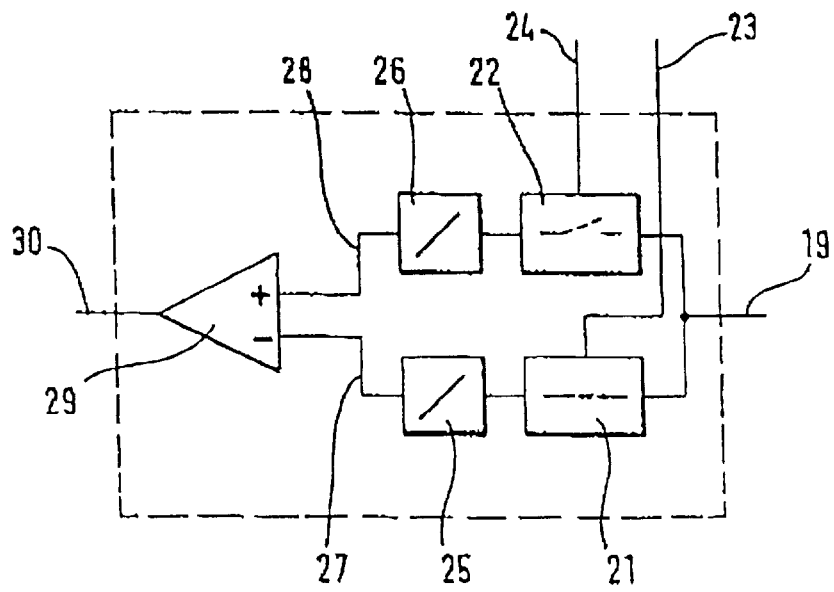
FIG. 2 is a detailed view of the signal processing state shown in FIG. 1.

The circuit design of the signal processing circuit 20 is illustrated in FIG. 2. The output signal 19 is sent to the inputs of two switches 21,22, which are alternately driven by switch supply lines 23,24 corresponding to the pulse signal or the inverted pulse signal. In this manner, the signal fraction of the output signal 19 provided by the first transmitter 10 is available at the output of the switch 21, and the signal fraction provided by the second transmitter 11 is available at the output of the switch 22. These signal fractions are integrated in outlet-connected integrators 25,26 and are sent as first and second output signals 27,28, respectively, to the inverting or non-inverting input of a differential amplifier 29. Due to the differential amplifier 29, the signal difference between the first and the second output signal 27 and 28 will be amplified with high sensitivity and output as an analog difference signal 30.

Therefore, the amplitude of the difference signal 30 is a measure of the difference between the quantities of light received from the first optical transmitter 10 and the second optical transmitter 11. Since the two optical transmitters 10,11 illuminate different regions of the window pane, the amplitude of the difference signal 30 represents a measure for local differences in the reflectivity and/or scattering behavior of the window pane.

The difference signal 30, as illustrated in FIG. 1, is sent to an A/D-converter 31 and is converted into a digital signal 32. The digital signal 32 is sent to a digital input 33 of the microcontroller 9.

The digital signal 32 is evaluated by the microcontroller 9 with respect to the signal amplitude and the temporal change in signal amplitude. The temporal change in the signal is used for recognition of different states of the window pane, such as may be caused, for example, by raindrops (fast changes), fine foggy mist (slow changes) or damage and adhered dirt (sudden, static changes). The information obtained from the microcontroller 9 is sent via a bidirectional data line 34 to a driver 36, which is connected over a serial data link on line 35 to an external data bus (not illustrated) of the motor vehicle.

A reset of the microcontroller 9 into a defined, initial state occurs when starting the motor vehicle by means of a control line 37 between the internal power supply 1 and the microcontroller 9. The initial state, as a rule, is a default value set by the manufacturer and can be reprogrammed by the user by means of the driver 36 and the bidirectional data lines 34, 35 as desired.

Figure 3:
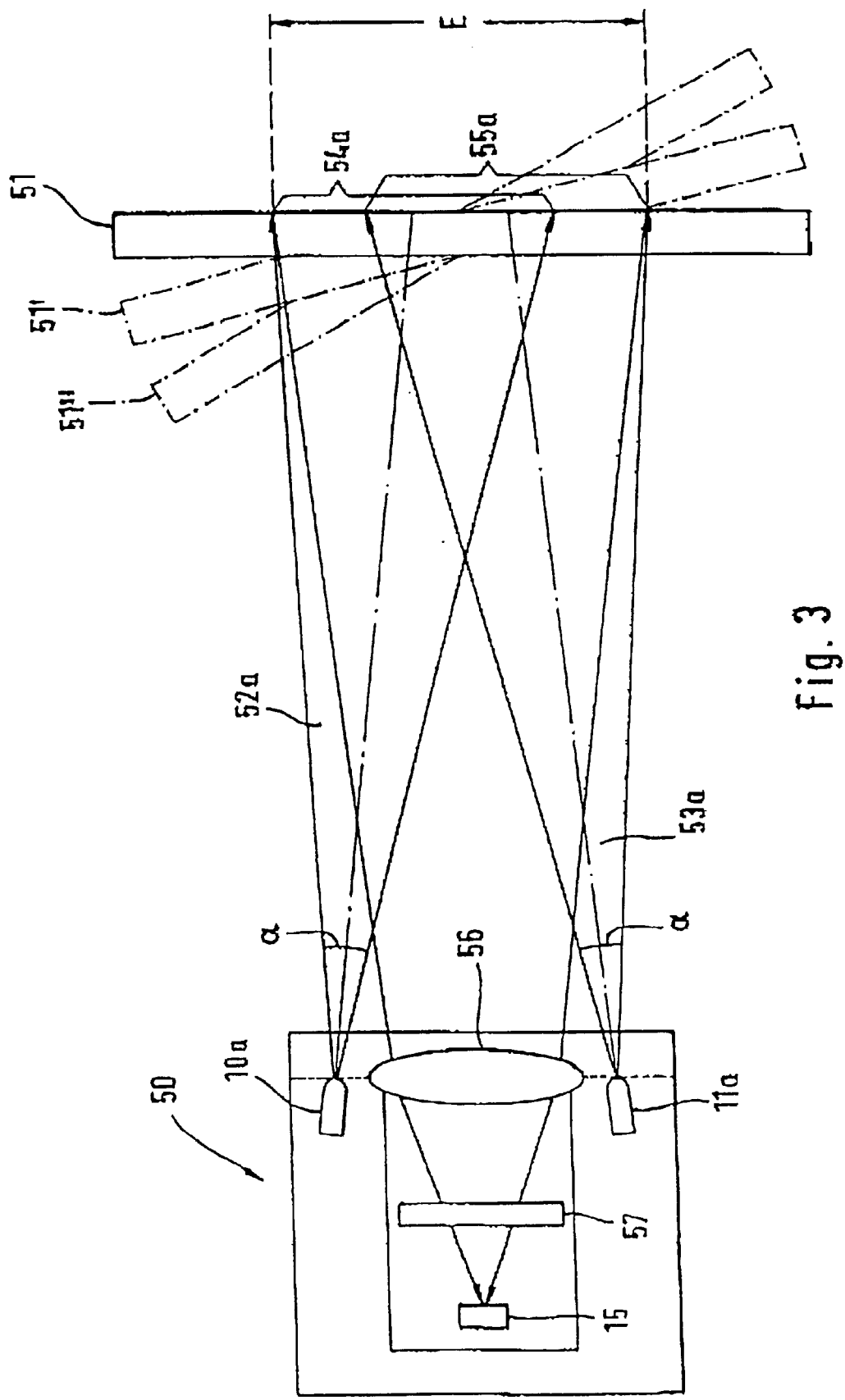
FIG. 3 is a first example of a transmitter/receiver device.

FIG. 3 shows a first example of a rain sensor module 50 and its positioning with respect to a window pane 51. The module 50 features as first optical transmitter, an IR-LED 10a and as second optical transmitter, an IR-LED 11a. The two IR-LEDs 10a, 11a generate illuminating light cones 52a and 53a each with identical opening angle α. The opening angle α can be defined by a suitable LED lens or additional lenses. FIG. 3 makes clear that the illuminating light cones 52a, 53a light up different light spots 54a, 55a on the window pane 51. The light spots 54a, 55a can partly overlap, as in the example illustrated in FIG. 3.

Furthermore, the module 50 has a reception lens 56, an optical IR-filter 57 and the IR receiver 15 already described in conjunction with FIG. 1. The receiver 15 is located on the optical axis of the reception lens 56 and is set at a distance from it. Due to the distance between the receiver 15 and the reception lens 56 and due to the power of the lens 56 and the shape of the lens 56, a reception zone E will be defined on the pane 51. Only reflected light (i.e., back-scattered or reflected) in the region of the reception zone E can be detected by the receiver 15.

The mode of operation of the module 50 is as follows: by means of the control of the IR-LEDs 10a and 11a explained in FIG. 1, the light spots 54a and 55a are illuminated alternately. The receiver 15 detects the scattered or reflected light coming back from the alternating two light spots 54a and 55a. Then, due to the switching structure described in FIG. 1, a possibly different reflection and scattering behavior of the pane 51 will be detected in the regions of the light spots 54a and 55a and evaluated with respect to temporal changes. Since the reception zone E of the two light spots 54a and 55a overlap, all lighted regions of the pane 51 contribute to a signal, so that a maximum light yield and thus a maximum sensitivity will be attained. Furthermore, the measuring sensitivity is also determined by the relative size of the light spots 54a and 55a to each other. In the case of light spots of identical size, a maximum sensitivity will be achieved, because in this case the signal tuning can be carried out with the greatest possible accuracy in the phase-synchronous demodulator formed of the switches 21, 22 and the integrators 25, 26.

In the case of a pane 51' or 51" located at an angle to the optical axis of the reception lens 56, basically comparable conditions are present, but with identical opening angles α of the LEDs, different sizes of the light spots 54a and 55a and also different distances from the receiver 15 are used. This situation can be taken into account by different configurations of the LEDs 10a, 11a with respect to their optics and/or lighting intensity, and also by an asymmetrical signal evaluation. Furthermore, it should be taken into account that, in the case of an inclined pane 51' or 51", reflected quantities of the reflected light will be increasingly reflected out of the beam path of the reception lens 56, which can be mostly compensated for by a suitable, axial and asymmetrical arrangement of the LEDs and also by a greater lighting intensity.

Figure 4:
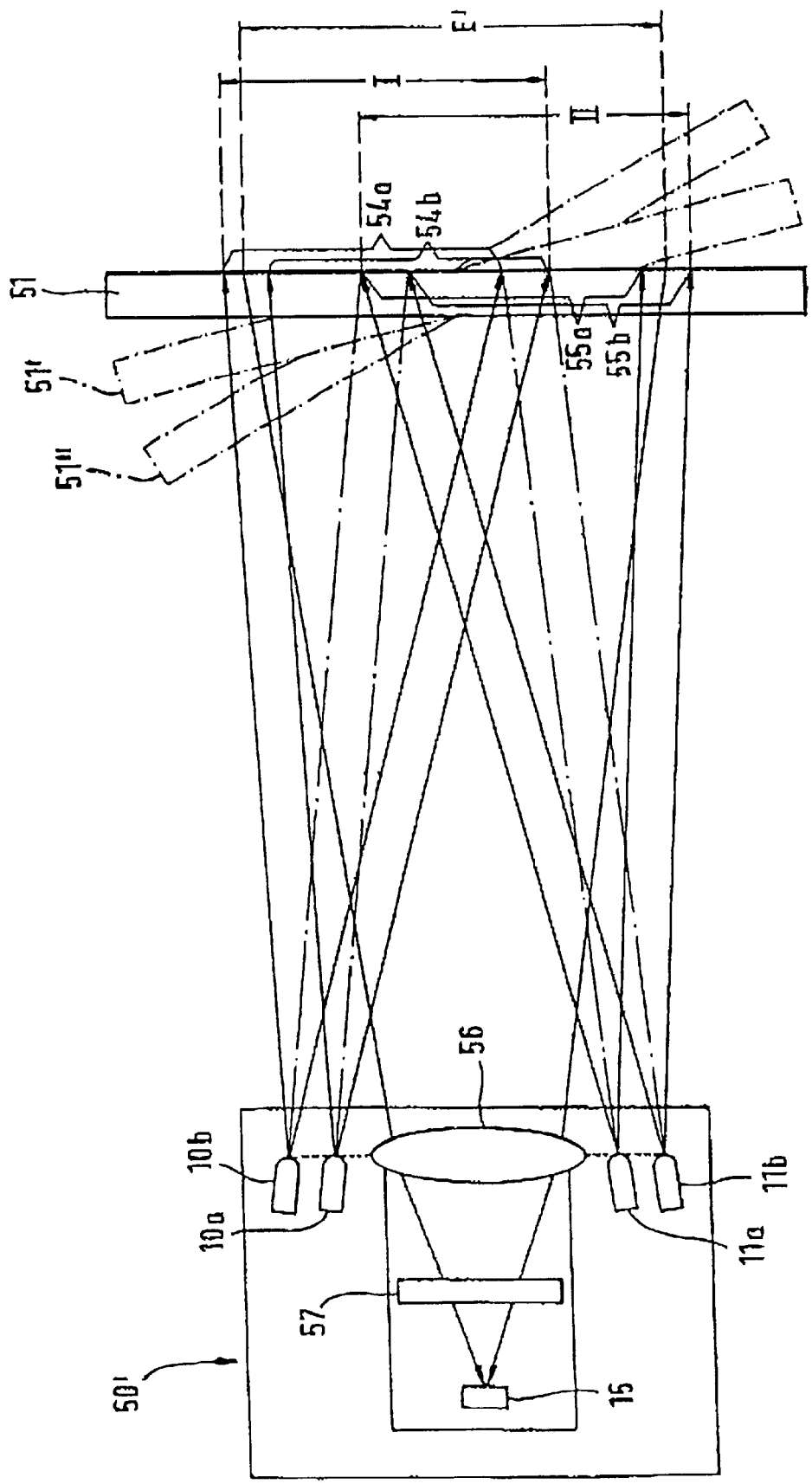
FIG. 4 is another example of a transmitter/receiver device.

FIG. 4 shows an example of a second module 50' with four IR-LEDs 10a, 10b and 11a, 11b. In this case, the IR-LEDs 10a, 10b and also the IR-LEDs 11a, 11b are jointly controlled according to FIG. 1. The light spots 54a, 54b generated by the jointly controlled IR-LEDs 10a, 10b together form a first illuminated zone I, while the light spots 55a, 55b of the IR-LEDs 11a, 11b are combined into a second illuminated zone II. A different reflection or scattering behavior of the pane 51 is measured in the illuminated zones I and II. In this case, the reception zone E' is located within the total lighting region formed by the two illuminated zones I and II.

Based on the increase in the number of IR-LEDs 10a, 10b, 11a, 11b in comparison to the first module 50 shown in FIG. 3, a greater distance between the rain sensor module 50' and the pane 51 is possible, and furthermore, a flatter angle can be used between the optical axis of the lens 56 and the pane 51', 51".

FIGS. 5, 6, 7 and 8 show various possibilities for lighting of the pane 51, and also the selection of the reception zone E.

Figure 5:
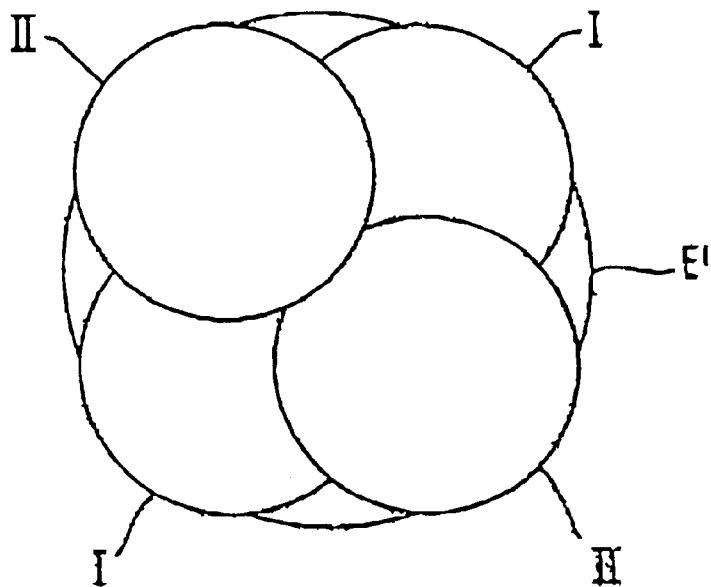
FIG. 5 is a representation of a first monitored region with an essentially square shape.

According to FIG. 5, four light spots form intersecting, diagonally arranged illuminated zones I and II. The reception zone E overlaps the overall illuminated zone I and II well.

Figure 6:
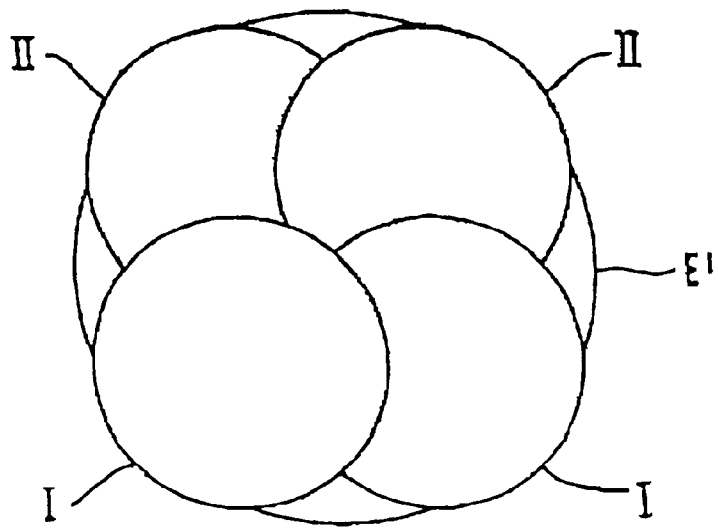
FIG. 6 is a representation of a second monitored region with an essentially square shape.

According to FIG. 6, two illuminated zones I and II located above each other are formed by four light spots. Here, too, there is a good overlap between the overall illuminated zone I and II anal the reception zone E.

The geometries shown in FIGS. 5 and 6 can be produced with the module 50' described in FIG. 4.

Figure 7:
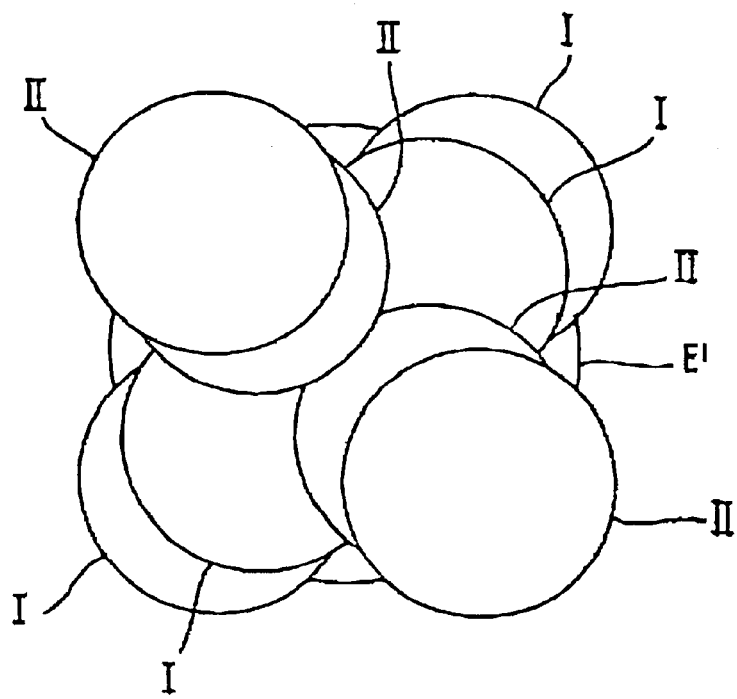
FIG. 7 is a representation of an additional monitored region with an essentially square shape.

FIG. 7 shows illuminated zones I and II, which are formed from a total of eight light spots. The illuminated zones I and II are arranged in a diagonal cross, similar to FIG. 5. The reception zone E' is configured in the shape of a circular disk as in FIGS. 5 and 6.

Figure 8:
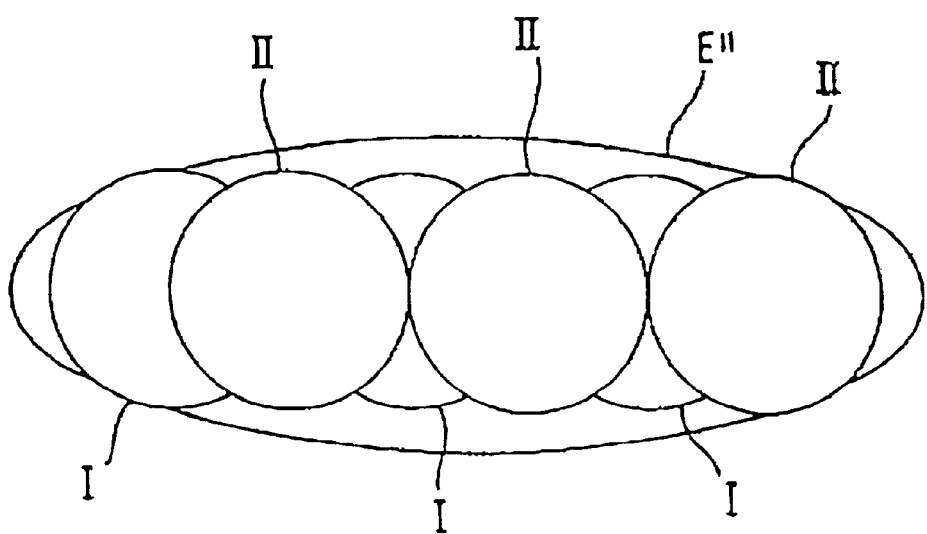
FIG. 8 is a representation of a monitored region with elongated shape.

In FIG. 8, the illuminated zones I and II are formed from six light spots located side by side, and neighboring light spots are allocated to different illuminated zones I or II. Here, the elliptical or cigar-shaped reception zone E" nearly circumscribes the entire illuminated surface and can be attained in a suitable manner by a combination of a spherical lens with a cylindrical lens, or by an astigmatic lens. The lighting geometry shown in FIG. 8 corresponds to the field of view of a driver of a motor vehicle, wherein the measured values can be ascertained in a highly accurate manner and thus control of the windshield wipers can be obtained.

In the case of abrasion, such as scratches on the window pane, the two areas detected by the sensor will not be identical. Therefore, in this case the transmitter regions I and II will not be alternated at a sensing ratio of 50:50, but rather of an asymmetrical sensing ratio of, e.g., 70:30. Due to the use of an integrated phase synchronous demodulator, this asymmetrical behavior can be taken into account.

Due to this variable sensing ratio, the sensor will thus compensate for faults, dirt and other static events. The sensor will recognize a change as static when it exceeds a characteristic time constant. lens, or by an astigmatic lens. The lighting geometry shown in FIG. 8 corresponds to the field of view of a driver of a motor vehicle, wherein the measured values can be ascertained in a highly accurate manner and thus a control of the windshield wipers can be obtained.

In the case of abrasion such as scratches on the window pane, the two areas detected by the sensor will not be identical. Therefore, in this case the transmitter regions I and II will not be alternated at a sensing ratio of 50:50, but rather of an asymmetrical sensing ratio of, e.g., 70:30. Due to the use of an integrated phase synchronous demodulator, this asymmetrical behavior can be taken into account.

Due to this variable sensing ratio, the sensor will thus compensate for faults, dirt and other static events. The sensor will recognize a change as static when it exceeds a characteristic time constant.

What is claimed is:

1. A device for monitoring the state of a window pane comprising a first optical transmitter which emits a first light beam onto a pane to illuminate a first region of the pane, a second optical transmitter which emits a second light beam onto a pane to illuminate a second region of the pane, at least one optical receiver which receives the light of the first and second light beams modulated by the first and second regions of the pane, respectively, and subsequently generates a reception signal, and an evaluation circuit that evaluates the reception signal to determine the state of the pane at the first and second regions of the pane, characterized in that the transmitters and the receiver are located at a distance from the pane and the evaluation circuit is composed of a discriminator stage which uses the reception signal to derive a first and a second reception signal according to the detected modulated light from at least one first optical transmitter and at least one second optical transmitter, respectively.

2. The device according to claim 1 characterized in that the light received by the receiver includes reflected or scattered light from the light beams.

3. The device according to claim 1 characterized in that the transmitters and the receiver are located at a distance of about 10 to 30 cm away from the pane.

4. The device according claim 1 characterized in that a light spot projected from a light beam onto the pane has a surface area of at least 25 cm$^2$.

5. The device according to claim 1 characterized in that the window pane is an automobile window pane and the state of the window pane is monitored in the region of the immediate field of view of a driver of the automobile.

6. The device according to claim 1 characterized in that the transmitter operates in the infrared range.

7. The device according to claim 1 characterized in that the device includes a single optical receiver which receives the light modulated by the pane from the light beams emitted from the optical transmitters.

8. A device for monitoring the state of a window pane including at least one optical transmitter which emits a light beam onto a pane, at least one optical receiver which receives the light of the light beam modulated by the pane and subsequently generates a reception signal, and an evaluation circuit that evaluates the reception signal to determine the state of the pane, characterized in that the at least one optical transmitter and the receiver are located at a distance from the pane, and the device is composed of a plurality of optical transmitters, and the evaluation circuit is composed of a discriminator stage which uses the reception signal to derive a first and a second reception signal according to the detected modulated light from at least one first optical transmitter and at least one second optical transmitter, wherein the first optical transmitters and second optical transmitters are controlled by a pulse signal of a different phase and the discriminator stage is formed of a phase-synchronous demodulator.

9. The device according to claim 1 characterized in that the evaluation circuit is composed of a difference stage which forms a difference signal from the first reception signal and the second reception signal.

10. The device according to claim 9 characterized in that the evaluation circuit is composed of a microcontroller that is supplied with the difference signal and that evaluates a temporal change in behavior of the difference signal.

11. The device according to claim 1 characterized by at least four optical transmitters whose light beams illuminate an essentially rectangular illuminated zone on the pane formed by partially overlapping light spots.

12. The device according to claim 1 characterized by at least three optical transmitters whose light beams illuminate an essentially elongated illuminated zone on the pane formed by partially overlapping light spots.

13. The device according to claim 1 characterized in that the transmitters and receiver are housed in a common housing.

14. The device according to claim 1 characterized in that on the input side of the optical receiver there is a reception lens which concentrates the light modulated by the pane onto the receiver.

15. The device according to claim 14 characterized in that the reception lens is designed so that a reception zone defined by the reception lens on the pane is adapted to the illuminated zone formed on the pane by the light spots of the light beam.

16. The device according to claim 14 characterized in that the reception lens is one of a spherical lens, a cylindrical lens and an astigmatic lens.

17. The device according to claim 1 characterized in that there is an optical filter on the input side of the optical receiver.

18. The device according to claim 1 characterized in that the at least one first optical transmitter and the at least one second optical transmitter are controlled by a pulse signal of a different phase and the discriminator stage is formed of a phase-synchronous demodulator.

19. The device according to claim 8 characterized by at least four optical transmitters whose light beams illuminate an essentially rectangular illuminated zone on the pane formed by partially overlapping light spots.

20. The device according to claim 8 characterized by at least three optical transmitters whose light beams illuminate an essentially elongated illuminated zone on the pane formed by partially overlapping light spots.

* * * * *